(12) United States Patent
Ünlü et al.

(10) Patent No.: US 7,110,118 B2
(45) Date of Patent: Sep. 19, 2006

(54) SPECTRAL IMAGING FOR VERTICAL SECTIONING

(75) Inventors: Selim M. Ünlü, Jamaica Plain, MA (US); Anna Swan, Cambridge, MA (US); Bennett B. Goldberg, Newton, MA (US); Stephen Ippolito, Tampa, FL (US); Lev Moiseev, Brighton, MA (US); Samuel Lipolf, Newton, MA (US); Yunjie Tong, Allston, MA (US)

(73) Assignee: Trustees of Boston University, Boston, MA (US)

( * ) Notice: Subject to any disclaimer, the term of this patent is extended or adjusted under 35 U.S.C. 154(b) by 468 days.

(21) Appl. No.: 10/451,096

(22) PCT Filed: Dec. 19, 2001

(86) PCT No.: PCT/US01/49391

§ 371 (c)(1),
(2), (4) Date: Jun. 18, 2003

(87) PCT Pub. No.: WO02/070984

PCT Pub. Date: Sep. 12, 2002

(65) Prior Publication Data

US 2004/0036884 A1 Feb. 26, 2004

Related U.S. Application Data

(60) Provisional application No. 60/256,574, filed on Dec. 19, 2000.

(51) Int. Cl.
*G01B 9/02* (2006.01)
(52) U.S. Cl. .................................. 356/450; 356/512
(58) Field of Classification Search ............... 356/450, 356/489, 495, 496, 498, 512

See application file for complete search history.

(56) References Cited

U.S. PATENT DOCUMENTS 4,374,120 A  2/1983  Soini et al. ............... 436/546

(Continued)

OTHER PUBLICATIONS

*Fluorescence Interferometry of Neuronal Cell Adhesion on Microstructured Silicon*; Dieter Braun, et al., Physical Review Letters, vol. 81, No. 23, Dec. 7, 1998, The American Physical Society, pp. 5241-5244.

(Continued)

*Primary Examiner*—Samuel A. Turner
(74) *Attorney, Agent, or Firm*—Weingarten, Schurgin, Gagnebin & Lebovici LLP

(57) ABSTRACT

A method and apparatus for performing optical microscopy in one to three dimensions employs a spectral self-interference fluorescent microscopy technique that includes providing at least one fluorescent microscopy sample, at least one objective lens, and at least one reflecting surface. The fluorescent sample is disposed between the objective lens and the reflecting surface, the distance from the sample to the reflecting surface being several to several tens times an excitation wavelength. Excitation light causes the fluorescent sample to emit light, at least a portion of which is reflected by the reflecting surface. The objective lens collects the reflected light and the light emitted directly by the fluorescent sample. The direct and reflected light interfere causing spectral oscillations in the emission spectrum. The periodicity and the peak wavelengths of the emission spectrum are spectroscopically analyzed to determine the optical path length between the fluorescent sample and the reflecting surface.

28 Claims, 6 Drawing Sheets

U.S. PATENT DOCUMENTS

| | | | |
|---|---|---|---|
| 5,641,629 A | 6/1997 | Pitner et al. | 435/6 |
| 5,650,275 A | 7/1997 | Pitner et al. | 435/6 |
| 5,731,153 A | 3/1998 | Lucas et al. | 435/6 |
| 5,741,658 A | 4/1998 | Hemstreet, III et al. | 435/6 |
| 5,976,466 A | 11/1999 | Ratner et al. | 422/82.11 |
| 6,038,041 A * | 3/2000 | Poon et al. | 359/1 |
| 6,040,191 A | 3/2000 | Grow | 436/172 |

OTHER PUBLICATIONS

*Fluorescence interference-contrast microscopy of cell adhesion on oxidized silicon*; d. Braun, et al., Department of Membrane and Neurophysics, Max-Planck-Institute for Biochemistry, Applied Physics A, Springer—Verlag 1997, pp. 341-348.

*Fluorescence interference-contrast microscopy on oxidized silicon using a monomolecular dye layer*; Armin Lambacher, et al, Department of Membrane and Neuropysics, Max-Planck-Institute for Biochemistry, May 22, 1996, Ap0plied Physics A, Springer-Verlag 1996, pp. 207-216.

*Enhancement of axial resolution in fluorescence microscopy of by standing-wave excitation*, Brent Balley, et al., Center for Light Microscope Imaging and Biotechnology and Departments of Biological Sciences and Physics, Carnegie Mellon University, Letters to Nature, vol. 366, Nov. 4, 1993, pp. 44-48.

\* cited by examiner

SPECTRAL IMAGING FOR VERTICAL SECTIONING

CROSS REFERENCE TO RELATED APPLICATIONS

This application claims priority of U.S. Provisional Patent Application No. 60/256,574 filed Dec. 19, 2000 entitled SPECTRAL IMAGING FOR VERTICAL SECTIONING.

STATEMENT REGARDING FEDERALLY SPONSORED RESEARCH OR DEVELOPMENT

This invention was made with Government Support under Contract Number DBI-9812377 awarded by the National Science Foundation, Contract Number 99-35201-8435 awarded by the U.S. Department of Agriculture and Contract Number JPL-1213572 awarded by DARPA. The Government has certain rights in the invention.

BACKGROUND OF THE INVENTION

The present invention relates generally to optical microscopy, and more specifically to optical microscopy in one to three dimensions that provides increased resolution while enhancing the specificity of optical measurements.

Techniques for performing optical microscopy are known that are capable of providing high resolution three-dimensional (3-D) imaging. Such optical microscopy techniques have a number of advantages over non-optical microscopy techniques such as electron microscopy and scanned probe microscopy. For example, optical microscopy can be used to view living tissue samples in their natural state, thereby enabling the study of complex biological mechanisms. In contrast, electron microscopy typically requires microscopy samples to be dried and exposed to a vacuum, which would normally kill living tissue samples. Not only can optical microscopy be used to view living tissue samples, but it can also be used to map the interior of such samples in multiple dimensions. Scanned probe microscopy, in comparison, can typically only be used to map surfaces of living tissue samples and is therefore incapable of providing information about the sample's interior. Optical microscopy can also be used with fluorescent probe technology to allow cellular components of living tissue samples to be identified and mapped with some degree of specificity.

Conventional techniques for performing 3-D optical microscopy include optical sectioning microscopy, scanning confocal microscopy, two-photon microscopy, and 4Pi confocal microscopy. Optical sectioning microscopy techniques typically comprise acquiring a series of images of a microscopy sample by successively moving sections of the sample through a focal plane. Each image includes in-focus information from the sample sections in the focal plane and out-of-focus information from the remaining sections of the sample. The image information is then analyzed by computer to reconstruct the 3-D structure of the sample. Such computer analysis typically employs at least one computational de-convolution algorithm and reference data describing the "blur" caused by a single point source of light. Scanning confocal microscopy techniques typically comprise focusing a laser beam onto a spot in a microscopy sample and detecting light through a pinhole focused onto the same spot in the sample as the laser. Next, the focal point is scanned in three dimensions through the sample. Finally, light intensity is detected as a function of the spot position to obtain a 3-D image of the sample.

However, conventional optical microscopy techniques such as optical sectioning microscopy and scanning confocal microscopy have drawbacks in that the depth resolution (i.e., the resolution in the vertical Z-direction) is, in general, worse than the resolution in the transverse (i.e., the X-Y) plane. As a result, the range of biological mechanisms that can be studied by these conventional optical microscopy techniques is limited.

For example, in order to study cellular functions such as cell cycle, development, motility, adhesion, and DNA replication, it is often necessary to perform precise 3-D localization of proteins within prokaryotic cells. This would normally require an optical microscopy technique capable of providing depth resolution on the order of at least ten to tens of nano-meters. However, conventional optical microscopy techniques such as optical sectioning microscopy and scanning confocal microscopy have traditionally only been capable of providing depth resolution on the order of half a micron.

It would therefore be desirable to have a technique for performing multi-dimensional optical microscopy that can be used, e.g., to study a wide range of biological mechanisms and sub-cellular processes in real time. Such an optical microscopy technique would provide resolution on the order of at least tens of nano-meters in at least one dimension. It would also be desirable to have an optical microscopy technique that can be used with fluorescent probe technology to enhance the specificity of optical measurements.

BRIEF SUMMARY OF THE INVENTION

In accordance with the present invention, a method and apparatus for performing optical microscopy in one to three dimensions is disclosed that can be used, e.g., to study a wide range of complex biological mechanisms. Benefits of the presently disclosed optical microscopy technique are achieved by employing spectral self-interference fluorescent microscopy to determine an optical path length between at least one fluorescent microscopy sample and a reflecting surface, employing variable standing wave illumination to extend the capabilities of the spectral self-interference fluorescent microscopy technique to provide vertical sectioning of an arbitrary distribution of fluorescent samples, and employing rotating aperture interferometric nanoscopy to provide such sectioning along a plurality of axes to generate image information suitable for reconstructing the three-dimensional structure of the sample distribution.

In one embodiment, the spectral self-interference fluorescent microscopy technique employed by the presently disclosed invention comprises providing at least one fluorescent microscopy sample, at least one objective lens, and a first reflecting surface. The fluorescent sample is disposed between the objective lens and the first reflecting surface. The fluorescent sample emits light, at least a portion of which is reflected by the first reflecting surface. The objective lens collects both the reflected light and the light emitted directly by the fluorescent sample. The direct and reflected light undergo constructive and destructive interference, thereby causing spectral oscillations or "fringes" in the emission spectrum. The difference between the respective optical path lengths of the direct and reflected light is such that only a relatively small change in wavelength is needed to transition between the constructive and destructive interference patterns. The periodicity and the peak wavelengths of the emission spectrum are then spectroscopically analyzed to determine the optical path length between the fluorescent sample and the first reflecting surface.

The spectral self-interference fluorescent microscopy technique is combined with variable standing wave illumination to allow the height determination capability of spectral self-interference fluorescent microscopy to be applied to an arbitrary vertical distribution of fluorescent samples. The variable standing wave illumination technique employed by the presently disclosed invention comprises configuring the first reflecting surface to reflect emission wavelengths and be transparent at an excitation wavelength, and providing a movable wavelength-independent reflecting surface configured to reflect the excitation wavelength. Excitation light is then provided by a light source and directed to the movable reflecting surface along a vertical axis, and the direct excitation light and the light reflected by the movable surface interfere to form at least one standing wave aligned in the direction of the vertical axis. Next, the movable reflecting surface is moved to translate the standing wave, thereby effectively scanning the vertical distribution of fluorescent samples through the standing wave. Such scanning causes fluorophores to emit light within a plurality of thin sections of the sample distribution orthogonal to the vertical axis.

The rotating aperture interferometric nanoscopy technique employed by the presently disclosed invention comprises directing the excitation light to the movable reflecting surface along a plurality of axes to form corresponding standing waves aligned in the directions of the respective axes. The plurality of axes includes the vertical axis and one or more axes at angles off the vertical axis. Next, the movable reflecting surface can be moved for sequentially translating the standing waves, thereby effectively scanning the fluorescent sample distribution through the standing waves. Such scanning causes fluorophores to emit light within respective pluralities of thin sections of the sample distribution, each plurality of sections being orthogonal to a respective axis. At least a portion of the light emitted in each section is reflected by the first reflecting surface, and both the reflected light and the light emitted directly by the respective sample sections are collected by the objective lens. The direct and reflected light associated with each sample section undergo constructive and destructive interference to cause fringes in the corresponding emission spectrum. Next, the periodicity and peak wavelengths of the respective emission spectra are spectroscopically analyzed to generate the image information, which is then tomographically analyzed to reconstruct the three-dimensional structure of the sample distribution.

By utilizing the techniques of spectral self-interference fluorescent microscopy, variable standing wave illumination, and rotating aperture interferometric nanoscopy, three-dimensional imaging of microscopy samples can be achieved with resolution on the order of at least ten to tens of nano-meters in one or more dimensions.

Other features, functions, and aspects of the invention will be evident from the Detailed Description of the Invention that follows.

BRIEF DESCRIPTION OF THE SEVERAL VIEWS OF THE DRAWING

The invention will be more fully understood with reference to the following Detailed Description of the Invention in conjunction with the drawings of which.

DETAILED DESCRIPTION OF THE INVENTION

U.S. Provisional Patent Application No. 60/256,574 filed Dec. 19, 2000 is incorporated herein by reference.

A method and apparatus for performing three-dimensional (3-D) optical microscopy with nano-meter scale resolution is provided. Such high resolution 3-D optical microscopy is achieved by employing spectral self-interference fluorescent microscopy to determine an optical path length between at least one fluorescent microscopy sample and a reflecting surface, employing variable standing wave illumination to extend the capabilities of the spectral self-interference fluorescent microscopy technique to provide vertical sectioning of an arbitrary distribution of fluorescent samples, and employing rotating aperture interferometric nanoscopy to provide such sectioning along a plurality of axes to generate image information suitable for reconstructing the three-dimensional structure of the sample distribution.

Figure 1:
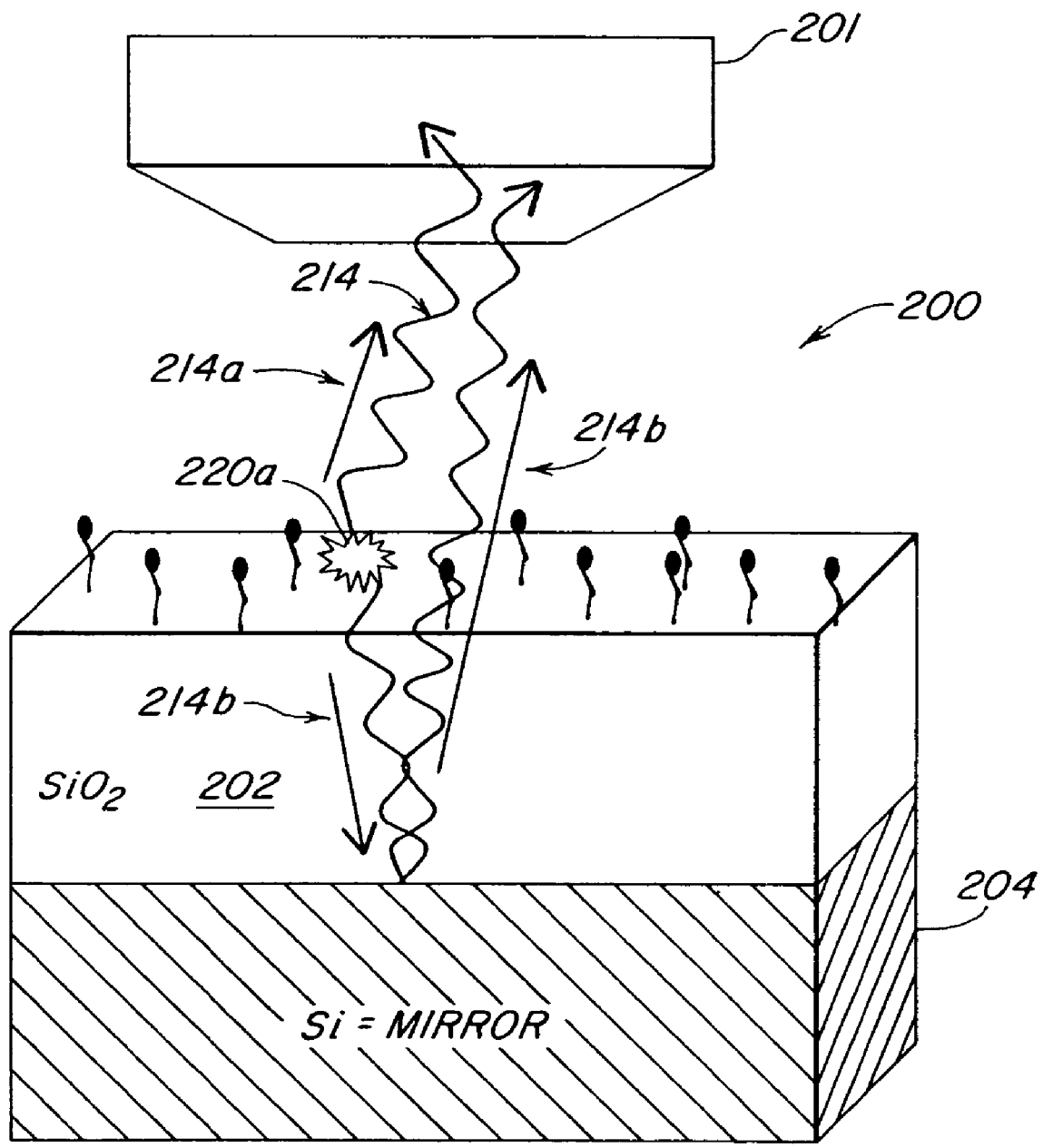
FIG. 1 is a conceptual representation of structure for performing spectral self-interference fluorescent microscopy according to the present invention.

The presently disclosed 3-D optical microscopy apparatus employs the spectral self-interference fluorescent microscopy technique to achieve one-dimensional imaging of at least one microscopy sample with nano-meter scale resolution. FIG. 1 depicts a conceptual representation of a device 200 configured to perform spectral self-interference fluorescent microscopy, in accordance with the present invention. In the illustrated embodiment, the device 200 includes a housing 201 configured to house at least one objective lens (not shown) for collecting light emitted by at least one first fluorescent microscopy sample 220a. As shown in FIG. 1, a first portion 214a of the light emitted by the fluorescent sample 220a travels directly from the sample 220a to the objective lens in the housing 201, while a second portion 214b of the emission light 214 travels to the housing 201 after being reflected by a first planar mirror 204. Accordingly, the objective lens in the housing 201 collects both the light 214a emitted directly by the fluorescent sample 220a and the light 214b reflected by the first mirror 204.

Those of ordinary skill in the art will appreciate that the emission light 214a emitted directly from the fluorescent sample 220a to the objective lens housing 201 and the emission light 214b reflected by the first mirror 204 can undergo constructive and destructive interference. In the illustrated embodiment, the difference between the respective optical path lengths of the direct and reflected light 214a and 214b is such that only a relatively small change in wavelength is needed to transition between constructive and destructive interference patterns. The interference between the direct and reflected emission light 214a and 214b forms at least one standing wave on the first mirror 204 that causes spectral oscillations or "fringes" in the corresponding emission spectrum.

Figure 2:
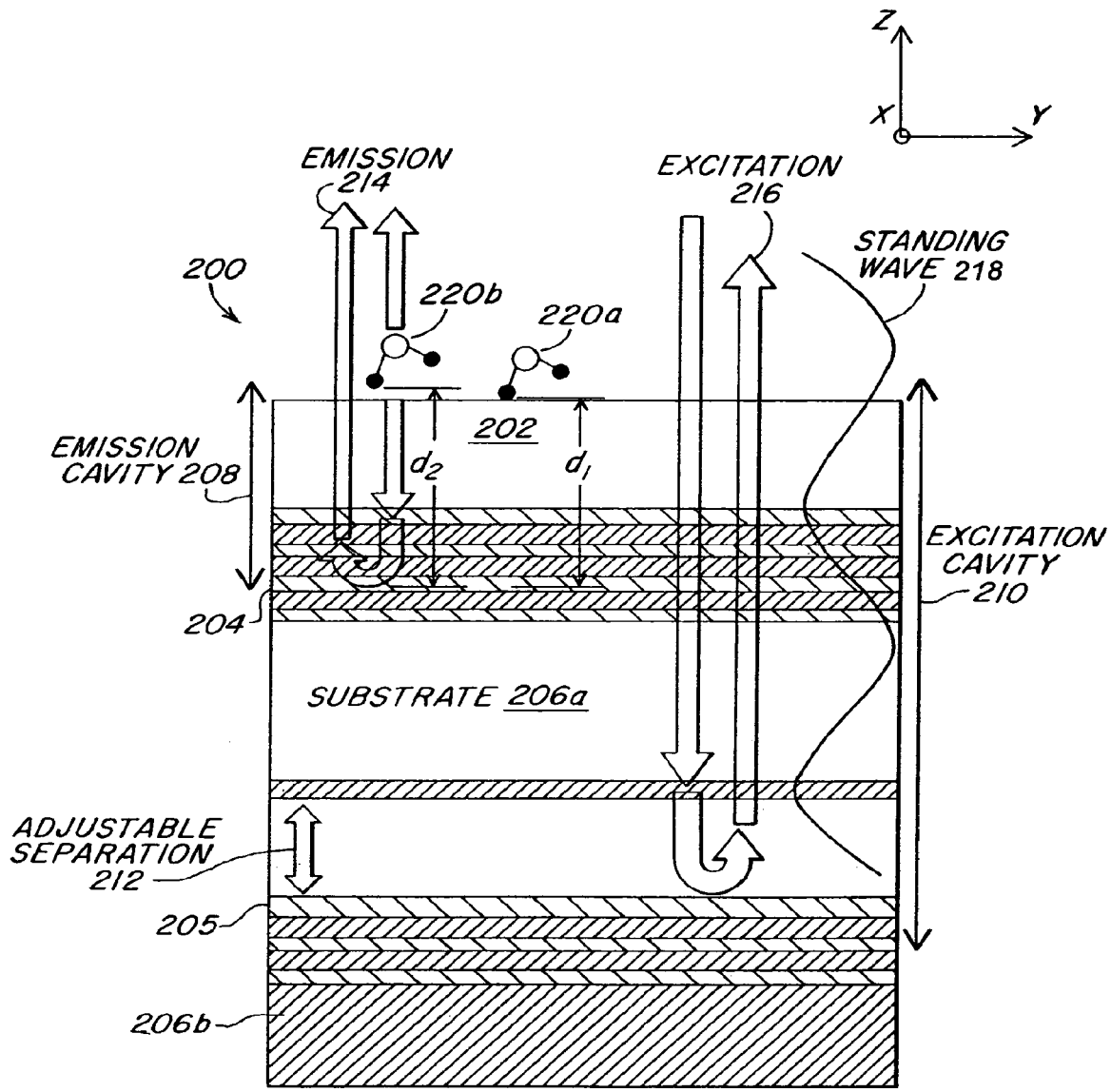
FIG. 2 is a detailed plan view of the structure conceptually represented in FIG. 1.

FIG. 2 depicts an illustrative embodiment of structure configured to implement the device 200 of FIG. 1. As shown in FIG. 2, the structure 200 may be implemented as a Micro Opto Electro Mechanical Systems (MOEMS) device. Specifically, the MOEMS device 200 includes a spacer 202 made of, e.g., silicon dioxide ($SiO_2$) and the first planar mirror 204 disposed on a silicon substrate 206a. The spacer 202 and the first mirror 204 are configured to form an emission cavity 208. FIG. 2 further shows the first microscopy sample 220a disposed at a predetermined distance $d_1$ from the first mirror 204 and a second microscopy sample 220b disposed at a predetermined distance $d_2$ from the mirror 204. For example, the microscopy sample 220b may be immobilized atop a cellular component such as a globular protein and the microscopy sample 220a may be immobilized directly on the surface of the spacer 202 using conventional microscopy sample immobilization techniques.

Because the illustrative spectral self-interference fluorescent microscopy technique employs fluorescent probe technology, the microscopy samples 220a and 220b are marked by suitable fluorescent probes. Further, a light source (not shown) may generate excitation light (generally shown at reference numeral 216) to illuminate the fluorescent samples 220a and 220b, thereby causing the samples 220a and 220b to emit light (generally shown at reference numeral 214). In the illustrated embodiment, the first mirror 204 is made of a wavelength selective dielectric configured to reflect the emission wavelengths while being transparent to the excitation wavelength. For example, the first mirror 204 may comprise $SiO_2$ and silicon nitride ($Si_3N_4$). In an alternative embodiment, the first mirror 204 may be made of material, e.g., silicon (Si), that reflects both the emission and excitation wavelengths. Moreover, the thickness of the spacer 202 is such that the respective distances $d_2$ and $d_1$ of the fluorescent samples 220a and 220b from the first mirror 204 are several to several tens times the wavelength of the excitation light 216. In the illustrated embodiment, the excitation wavelength ranges from about 500 to 600 nano-meters.

Figure 3:
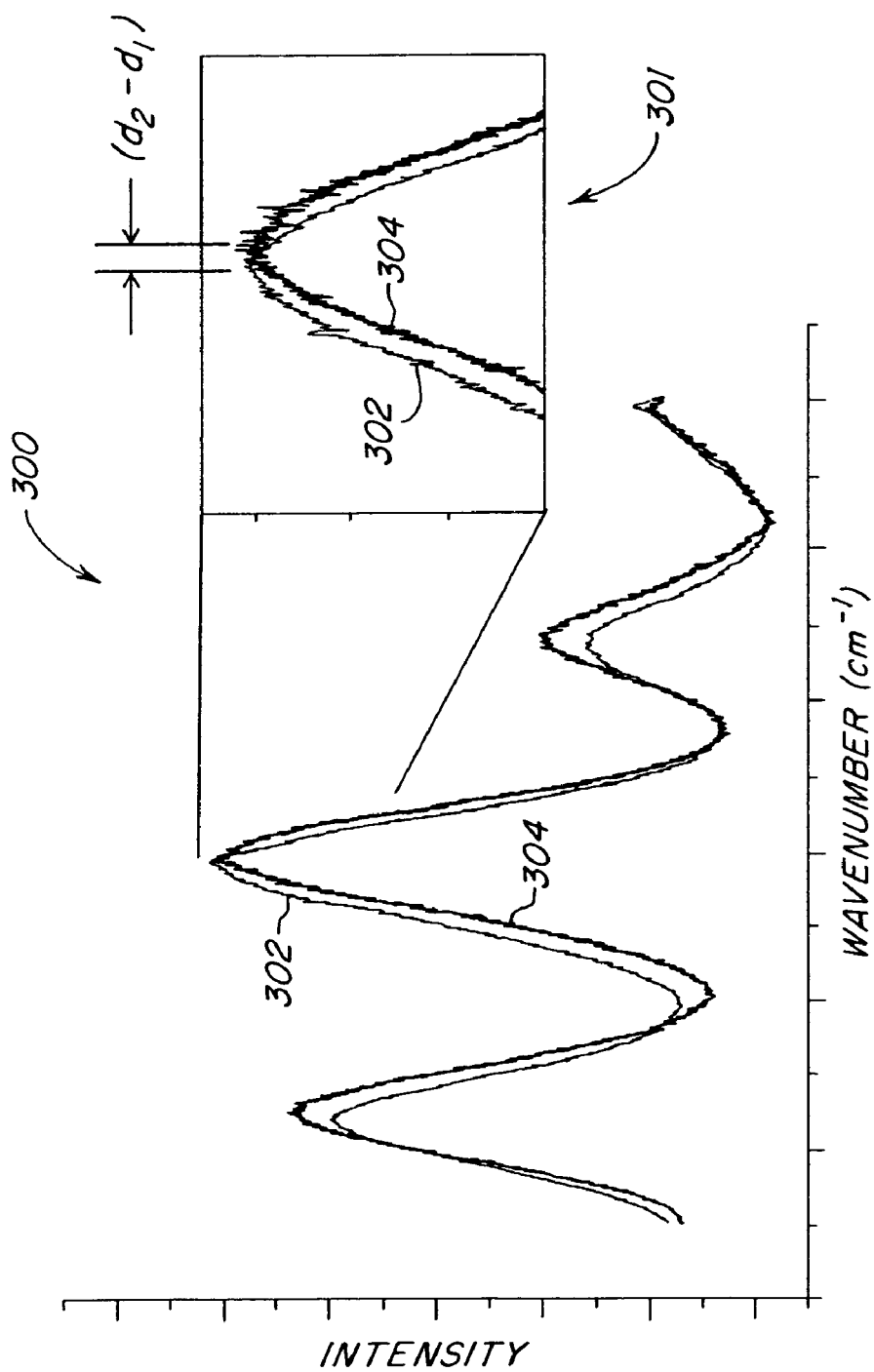
FIG. 3 is a diagram depicting emission spectra corresponding to microscopy samples disposed at respective distances from a reflecting surface included in the structure of FIG. 2.

FIG. 3 depicts exemplary emission spectra 300 associated with the fluorescent samples 220a and 220b (see FIG. 2). For example, the emission spectrum 302 may be associated with the fluorescent sample 220b immobilized at the predetermined distance $d_2$ from the first mirror 204, and the emission spectrum 304 may be associated with the fluorescent sample 220a immobilized at the predetermined distance $d_1$ from the first mirror 204 (i.e., on the surface of the spacer 202). As shown in FIG. 3, both emission spectra 302 and 304 comprise fringes caused by constructive and destructive interference between direct and reflected light emitted by the fluorescent samples 220a and 220b, respectively. These spectral fringes impart periodic behavior to the emission spectra 302 and 304, the details of which may be extracted using conventional mathematical techniques.

It is noted that the periodicity and peak wavelengths of the respective emission spectra 302 and 304 are functions of the distances $d_2$ and $d_1$ between the fluorescent samples 220a and 220b and the first mirror 204, respectively, and possibly the orientation of the samples 220a and 220b relative to the mirror 204. In effect, information relating to the respective distances $d_2$ and $d_1$ is encoded in the emission spectra 302 and 304. It is further noted that the distance information encoded in the emission spectra 302 and 304 is independent of the fluorescent sample density, the emission intensity, and the excitation field strength. By analyzing the intensity peaks and valleys in the emission spectra 302 and 304, the location of the fluorescent sample responsible for the respective emission signal can be precisely determined, and a high level of discrimination between the specifically bound fluorescent sample 220b and the surface bound fluorescent sample 220a can be achieved.

For example, differential phase measurements may be performed using the emission spectra 300 to discriminate between the surface bound and specifically bound microscopy samples 220a and 220b. Such a phase difference is illustrated in a detail view 301 (see FIG. 3) of respective intensity peaks in the emission spectra 302 and 304. By measuring the magnitude of this phase difference, the difference ($d_2$–$d_1$) between the respective distances from the fluorescent samples 220a and 220b to the first mirror 204 can be determined with nano-meter scale resolution.

It is understood that the respective distances between the fluorescent samples 220a and 220b and the first mirror 204 may also be determined using direct phase measurements. Moreover, the first mirror 204 may be moved along an axis passing near or through at least one of the samples 220a and 220b to cause the pattern of intensity of light in the emission spectra 302 and 304 to shift as a function of wavelength. For example, the location of the first mirror 204 may be controlled relative to the fluorescent samples 220a and 220b by a piezo-electric tube scanner.

The presently disclosed spectral self-interference fluorescent microscopy technique will be better understood with reference to the following first illustrative example. In this first example, the spectral self-interference microscopy technique is performed by the MOEMS device 200 (see FIG. 2) to determine the respective distances $d_2$ and $d_1$ from the fluorescent samples 220a and 220b to the first mirror 204, which is configured to reflect the emission wavelengths and be transparent to the excitation wavelength. For example, the fluorescent samples 220a and 220b may be respective bio specimens comprising living tissue.

Specifically, the fluorescent sample 220b is immobilized at the predetermined distance $d_2$ from the first mirror 204 while the fluorescent sample 220a is immobilized at the predetermined distance $d_1$ from the first mirror 204, i.e., directly on the surface of the spacer 202. It is noted that the thickness of the spacer 202 is several to several tens times the excitation wavelength. Each fluorescent sample 220a and 220b emits light in response to being illuminated by the excitation light, and the emission spectrum associated with each fluorescent sample 220a and 220b is distinguishable by its periodicity and peak wavelengths (i.e., by its frequency and phase).

In this first example, the respective emission spectra associated with the fluorescent samples 220a and 220b add together to form a complex emission spectrum representative of the sum of the individual emissions. Because each emission spectrum is distinguishable by its frequency and phase, conventional Fourier Transform techniques can be used to calculate the amplitudes and frequencies of the spectra components. Specifically, the complex emission spectrum comprises a plurality of components, one of which creates the spectral fringe pattern and holds all of the distance information. As explained above, the fringe pattern is given by the interference of the emission light with its reflection from the first mirror 204. The interference component of the intensity for each emitting sample 220a and 220b is given by $$|1+re^{-ik_02(nD+d)}|^2 = 1+r^2+2r\cos(k_02(nD+d)), \quad (1)$$

in which "r" is the total reflectivity of the first mirror 204, "nD" is the respective optical path in the spacer 202, and "d" is the distance of the fluorescent sample from the first mirror 204. It is noted that the intensities of the fluorescent samples 220a and 220b are added because they are incoherent. Further, each of the fluorescent samples 220a and 220b makes a unique contribution to the complex emission spectrum.

The calculated frequency and phase information for the respective emission spectra are indicative of the respective distances $d_2$ and $d_1$ of the samples 220a and 220b from the first mirror 204 while the calculated amplitudes correspond to the fluorescent density at those distances. It is noted that such complex emission spectra can be suitably de-convoluted to allow distances between emitting microscopy samples and reflecting surfaces to be determined with a resolution of at least ten to tens of nano-meters.

The presently disclosed 3-D optical microscopy apparatus employs the variable standing wave illumination technique to extend the capabilities of spectral self-interference microscopy to provide vertical sectioning of an arbitrary distribution of fluorescent samples. To this end, the MOEMS device 200 (see FIG. 2) further includes a movable planar mirror 205 disposed on a silicon substrate 206b and configured to reflect the excitation light 216. For example, the movable mirror 205 may be a broadband mirror comprising suitable metal and dielectric layers. In the illustrated embodiment, the spacer 202, the first mirror 204 (which is transparent to the excitation light 216), the substrate 206a, and the movable mirror 205 are configured to form an excitation cavity 210. It is noted that the excitation cavity 210 comprises an adjustable separation 212 between the substrate 206a and the movable mirror 205. For example, the separation 212 in the MOEMS device 200 may be adjusted by controlling the location of the movable mirror 205 relative to the substrate 206a using a piezo-electric tube scanner.

As described above, the excitation light 216 is directed to the fluorescent samples 220a and 220b, thereby causing the samples 220a and 220b to emit the emission light 214. The excitation light 216 is further transmitted through the first mirror 204 to the movable mirror 205 along the Z-axis. The direct excitation light 216 and the excitation light 216 reflected by the movable mirror 205 interfere to form at least one standing wave 218 on the movable mirror 205 aligned in the Z-direction. By moving the mirror 205 along the Z-axis, the standing wave 218 can be translated for effectively scanning a fluorescent sample distribution including the fluorescent samples 220a and 220b through the standing wave 218. It is understood that such translation of the standing wave 218 may also be performed by varying either the angle of the excitation light 216 or the excitation wavelength.

Figure 7:
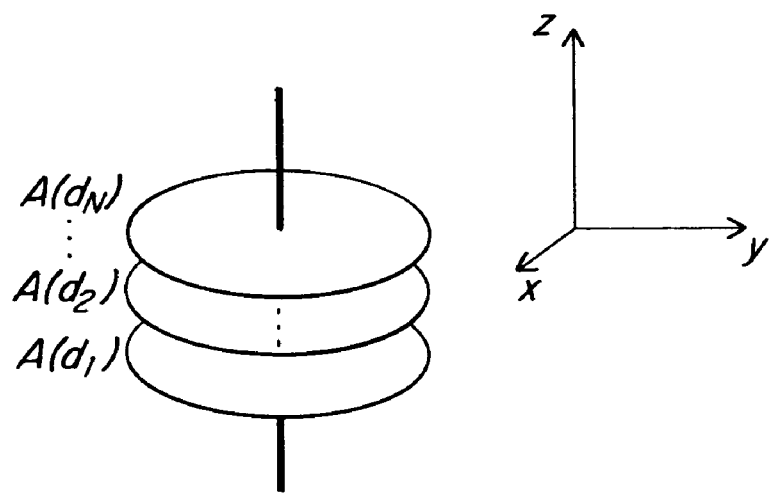
FIG. 7 is a conceptual representation of vertical sectioning of a microscopy sample employed by the apparatus of FIG. 4.

Scanning the distribution of fluorescent samples through the field of the standing wave 218 causes fluorophores to emit light within a plurality of thin sections of the sample distribution orthogonal to the Z-axis, as shown in the conceptual representation of FIG. 7. In the illustrated embodiment, the spatial variation of the incident field intensity excites the fluorophores within the thin sample sections to attain a resolution of at least ten to tens of nano-meters along the Z-axis.

The presently disclosed variable standing wave illumination technique will be better understood with reference to the following second illustrative example. In this second example, variable standing wave illumination is used in conjunction with the above-described spectral self-interference fluorescent microscopy technique to determine the location of at least one broad continuous distribution of fluorescent samples.

Specifically, a distribution of fluorescent samples such as the samples 220a and 220b (see FIG. 2) are immobilized at predetermined distances (i.e., at least several to several tens times the excitation wavelength) from the first mirror 204. The fluorescent samples emit light in response to being illuminated by the excitation light, and the emission spectra associated with the respective samples are distinguishable by their frequency and phase. Moreover, the excitation light is reflected by the movable mirror 205 to create at least one standing wave 218 aligned in the Z-direction.

In this second example, the movable mirror 205 is moved along the Z-axis to scan the distribution of fluorescent samples through the standing wave 218. In effect, the standing wave 218 is used to obtain thin sections of the sample distribution, thereby discretizing the broad distribution of fluorophores. Specifically, the distribution of the fluorophores can be represented by profiles $A(d_1) \ldots A(d_N)$ (see FIG. 7), which comprise a discrete series of axial slices at distances $d_1$ to $d_N$ from the first mirror 204. Unknown emission amplitudes corresponding to each slice $A(d_1) \ldots A(d_N)$ can be determined from a set of spectra measured as the standing wave 218 is scanned. In this example, such measured spectra are expressed as $$S_j = \Sigma_{(i=1-N)} I_j(d_i) A_i^2 [1 + R^2 + 2R\cos(2k(nD+d_i))], \quad (2)$$

$$S_j = \Sigma_{(i=1-N)} I_j(d_i) A_i^2 F_i, \quad (3)$$

in which "$F_i$" is an interference term, "$I_j(d_i)$" is the strength of the excitation intensity at distance "$d_i$" for standing wave position "j", "$S_j$" is the entire observed spectrum, and "$A_i$" is the emission amplitude from position $d_i$. Collecting observations from N different excitation standing wave field positions yields $$\begin{bmatrix} S_1(k) \\ S_2(k) \\ \vdots \\ S_N(k) \end{bmatrix} = \begin{bmatrix} I_1(d_1)F_1 & I_1(d_2)F_2 & \ldots & I_1(d_N)F_N \\ I_2(d_1)F_1 & I_2(d_2)F_2 & \ldots & I_2(d_N)F_N \\ \vdots & & & \vdots \\ I_N(d_1)F_1 & I_N(d_2)F_2 & \ldots & I_N(d_N)F_N \end{bmatrix} \begin{bmatrix} A_1^2 \\ a_2^2 \\ \vdots \\ A_N^2 \end{bmatrix} \quad (4)$$

which may be solved to recover the fluorophore distribution profiles $A(d_1) \ldots A(d_N)$.

It is noted that the determination of the vertical distribution of the fluorescent samples can be facilitated by immobilizing one or more samples at predetermined reference distances (i.e., at least several to several tens times the excitation wavelength) from the first mirror 204 for use in providing a more complete basis set for subsequent de-convolution of the emission spectra.

Figure 4:
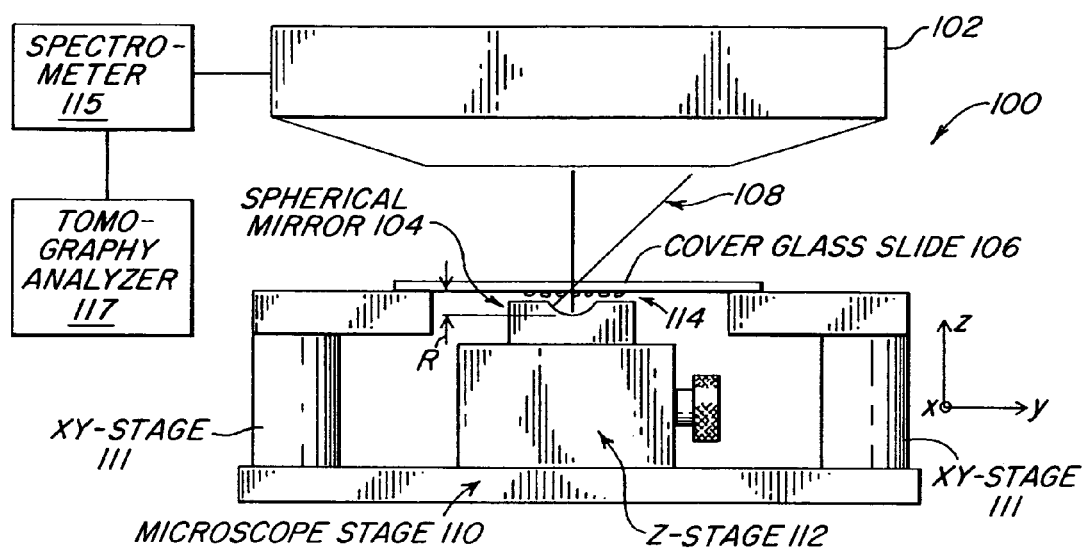
FIG. 4 is a plan view of an apparatus for performing three-dimensional optical microscopy according to the present invention.

FIG. 4 depicts an illustrative embodiment of an apparatus 100 for performing high resolution 3-D optical microscopy, in accordance with the present invention. The optical microscopy apparatus 100 includes a housing 102 configured to house a light source 105 (see FIG. 5) and first and second objective lenses 101 and 103 (see FIGS. 5 and 6), a spherical mirror 104, and a plurality of microscope stages 110–112. The light source 105 is configured to generate excitation light 108, and the objective lenses 101 and 103 are configured to direct the excitation light 108 to a microscopy specimen ("sample") 114 and collect light emitted by the sample 114 in response to being illuminated by the excitation light 108. In the illustrated embodiment, the light source 105 is a single mode optical fiber and the excitation light 108 comprises laser radiation in the form of a Gaussian beam. Further, each of the objective lenses 101 and 103 have a relatively high Numerical Aperture (e.g., NA≈0.87). The optical microscopy apparatus 100 is coupleable to a spectrometer 115 configured to generate image data from spectral information collected via the objective lenses 101 and 103. For example, the spectrometer 115 may comprise a grating spectrometer. Further, the spectrometer 115 may provide the image data to a tomography analyzer 117 configured to tomographically analyze the image data for reconstructing the three-dimensional structure of the microscopy sample 114.

As shown in FIG. 4, the microscopy sample 114 is mounted on at least one glass cover slide 106, which is directly supported by the XY-stage 111. Further, the spherical mirror 104 is directly supported by the Z-stage 112. The XY-stage 111 is configured for adjustably positioning the glass cover slide 106 in the XY-plane to place the microscopy sample 114 mounted thereon at the focal point of the excitation light 108, and the Z-stage 112 is configured for adjustably positioning the spherical mirror 104 in the Z-direction to place the center of the mirror 104 at the approximate location of the sample 114.

The optical microscopy apparatus 100 (see FIG. 4) employs the rotating aperture interferometric nanoscopy technique to provide sectioning of an arbitrary distribution of fluorescent samples including the microscopy sample 114 along a plurality of axes to generate image information suitable for reconstructing the 3-D structure of the sample distribution. For example, the plurality of axes may include the vertical Z-axis and one or more axes disposed at angles off the vertical axis.

Figure 5:
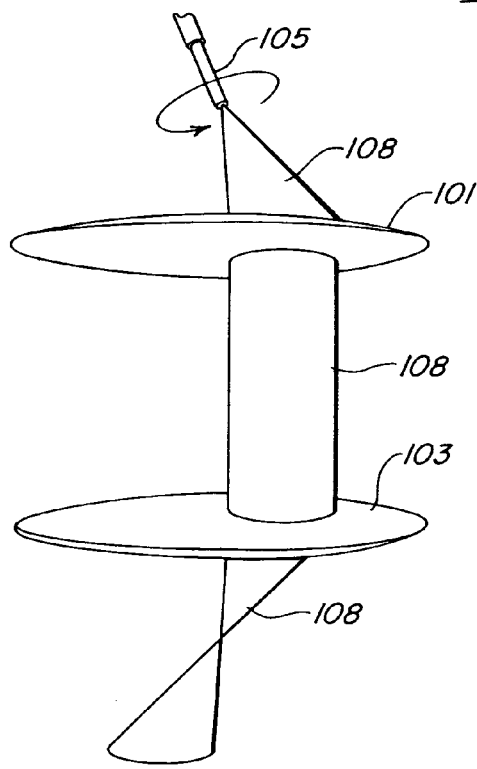
FIG. 5 is a conceptual representation of a technique for coupling a light beam to off-axis angles employed by the apparatus of FIG. 4.

FIG. 5 depicts the light source 105 and the objective lenses 101 and 103 of the optical microscopy apparatus 100 (see FIG. 4) arranged to provide the excitation light 108 at an exemplary off-axis angle. It is noted that different angles of the excitation light 108 can be attained by varying the angle of the light source 105 relative to the XY-plane and/or rotating the light source 105, as shown in FIG. 5.

In the illustrated embodiment, the light source 105, (i.e., the single mode optical fiber) is, in effect, placed at the center of a conjugate image plane of a 4f microscope confocal system. Further, the objective lenses 101 and 103 are identical and arranged to reproduce the excitation light 108 provided by the light source 105 at the location of the microscopy sample 114. In this way, the excitation light 108 is optimally coupled in a single optical mode from the light source 105 to the microscopy sample 114, and subsequently optimally collected from the same mode in emission.

Having provided the excitation light 108 to the microscopy sample 114 at the desired angle, the light 108 is reflected back onto itself by the spherical mirror 104 to create the excitation standing wave 218 (see FIG. 2). In the illustrated embodiment, the spherical mirror 104 is positioned by the Z-stage 112 at a distance R (see FIG. 4) from the microscopy sample 114 that matches spherical phase wave fronts 109 (see FIG. 6). Specifically, the mirror 104 is configured with a radius that is greater than the confocal parameter so that the phase wave fronts 109 are spherical at the position of the mirror 104. In this configuration, light emitted below the focal plane at all angles by a given fluorophore within the microscopy sample 114 is reflected back to that fluorophore such that the direct and reflected light travel exactly the same optical path.

As a result, the spherical phase wave fronts 109 emitted below the focal plane are reflected back to the point of origin, thereby removing any angular dependence of the phase difference between the direct and reflected emission light. It is noted that the polarization is also mapped back onto itself without distortion. It is expected that use of the spherical mirror 104 matched to the phase wave fronts 109 and the objective lenses 101 and 103 having relatively high NA will increase the lateral resolution of the optical microscopy apparatus 100 to at least ten to tens of nano-meters. In contrast, conventional optical microscopy apparatus normally provide diffraction limited lateral resolution, which is typically on the order of hundreds of nano-meters.

Figure 6:
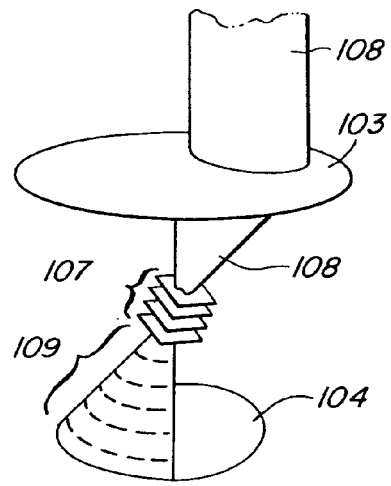
FIG. 6 is a conceptual representation of rotating aperture interferometric nanoscopy providing sectioning of a microscopy sample along an off-axis angle employed by the apparatus of FIG. 4.
Figure 8:
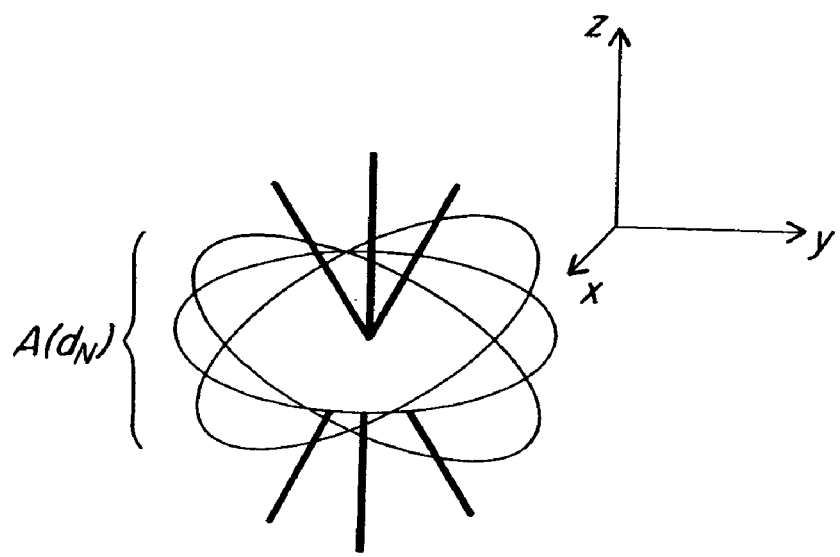
FIG. 8 is a conceptual representation of sectioning of a microscopy sample along a plurality of axes employed by the apparatus of FIG. 4.

As required in the variable standing wave illumination technique, the spherical mirror 104 is moved to translate the excitation standing wave 218 for effectively scanning the distribution of fluorescent samples along the vertical axis and at the off-axis angles. As mentioned above, the movement of the spherical mirror 104 may be piezo-electrically controlled. Such scanning of the fluorescent sample distribution through the field of the standing wave 218 causes fluorophores to emit light within a plurality of thin sample sections orthogonal to the plurality of axes. This is shown in the conceptual representation of FIG. 8, in which the distribution of the fluorophores is represented by at least one profile $A(d_N)$. FIG. 6 depicts another conceptual representation of emitting fluorophores within a plurality of thin sample sections 107 at an exemplary off-axis angle. These exemplary fluorophore distribution profiles comprise image information that can be spectroscopically and tomographically analyzed to reconstruct the three-dimensional structure of the sample distribution. It is noted that the spatial variation of the incident field intensity excites the fluorophores within the thin sample sections to attain a resolution of at least ten to tens of nano-meters along the respective axes. Moreover, the use of the spherical mirror 104 matched to the phase wave fronts and the high NA objective lenses 101 and 103 increases lateral resolution in planes orthogonal to the respective axes to at least ten to tens of nano-meters.

Figure 9:
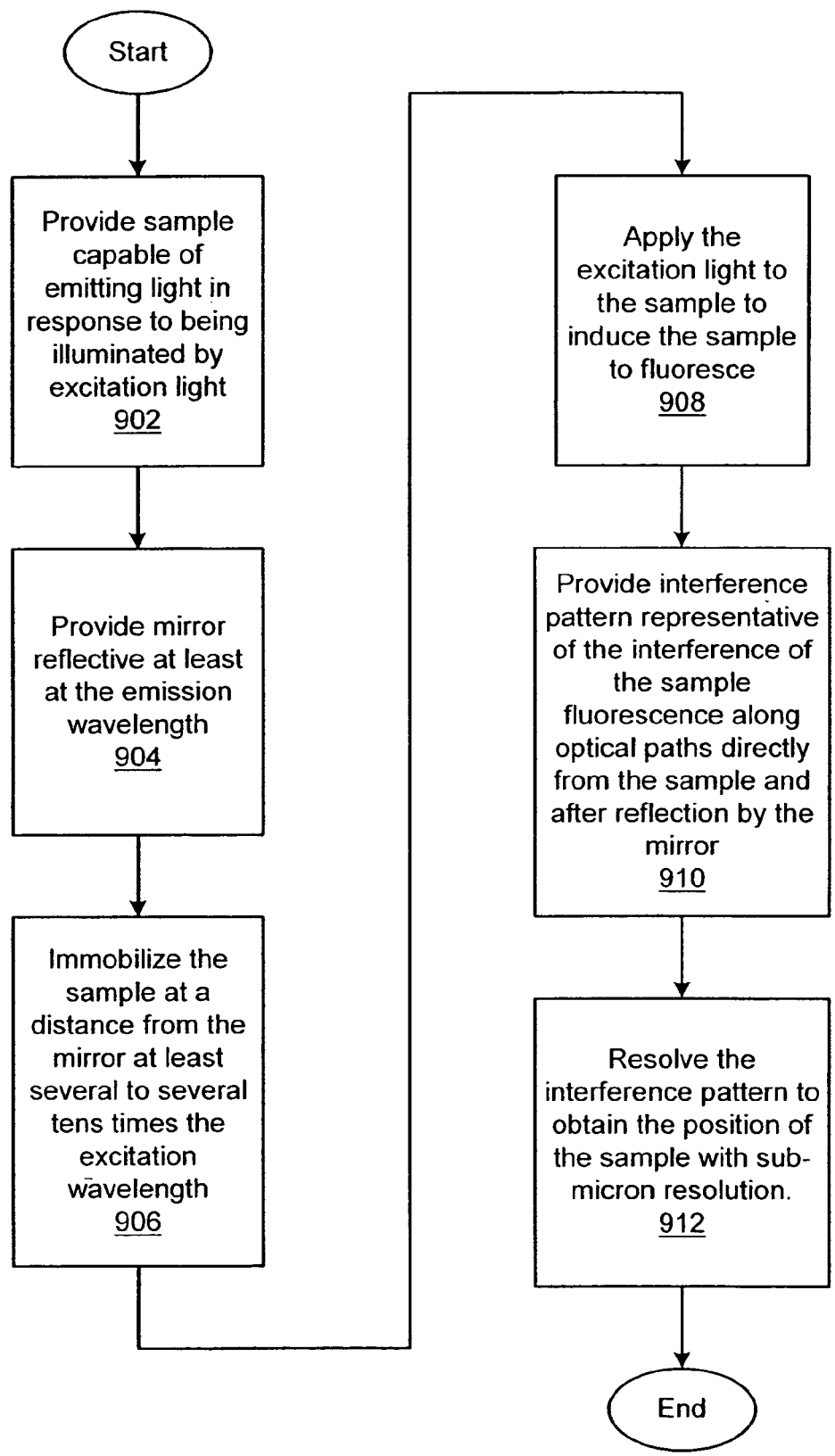
FIG. 9 is a flow chart depicting a method of performing three-dimensional optical microscopy according to the present invention.

The presently disclosed method of performing 3-D optical microscopy is illustrated by reference to FIG. 9. As depicted in step 902, a fluorescent microscopy sample is provided that is capable of emitting light in response to being illuminated by excitation light. Next, a mirror is provided, as depicted in step 904, that is reflective at least at the emission wavelength. The microscopy sample is then immobilized, as depicted in step 906, at a distance from the mirror that is at least several to several tens times the excitation wavelength. Next, the excitation light is applied, as depicted in step 908, to the microscopy sample to induce the sample to fluoresce. An interference pattern is then provided, as depicted in step 910, representative of the interference of the sample fluorescence along optical paths directly from the sample and after reflection by the mirror. Finally, the interference pattern is resolved, as depicted in step 912, to obtain the position of the microscopy sample with sub-micron resolution.

It will further be appreciated by those of ordinary skill in the art that modifications to and variations of the above-described multi-dimensional optical microscopy technique may be made without departing from the inventive concepts disclosed herein. Accordingly, the invention should not be viewed as limited except as by the scope and spirit of the appended claims.

What is claimed is:

1. Apparatus for determining the position of at least one specimen in an environment, comprising:
   at least one first surface reflective at least at a wavelength range of interest;
   said first reflective surface being disposed at a predetermined distance from said specimen;
   said specimen having light emission associated therewith; and
   a spectral analyzer responsive to light representing an interference of the specimen emission associated with said at least one specimen on paths directly from said at least one specimen and after reflection by said first reflective surface to provide an interference pattern resolvable for position of said specimen.

2. The apparatus of claim 1 wherein said spectral analyzer includes at least one lens directing radiation from said specimen to said spectral analyzer.

3. The apparatus of claim 2 further including a source of radiation for said specimen to excite said emission of said specimen.

4. The apparatus of claim 3 wherein said source applies said radiation through at least one lens.

5. The apparatus of claim 1 wherein said specimen emissions are characterized by one or more of spontaneous emission, excitation induced emissions, self emissions of said specimen, and decaying emissions from previously excited emissions.

6. The apparatus of claim 3 further including a second reflective surface distant from said first reflective surface, said first reflective surface being disposed between said second reflective surface and said specimen, said second surface being reflective at a wavelength of said source and said first surface being transmissive at the wavelength of said source.

7. The apparatus of claim 6 wherein:
   means are provided for moving at least one of said first and second reflective surfaces; and
   said spectrum analyzer includes means for moving an angle of view through which said analyzer responds to said emission and for providing a tomographic representation of the environment of said specimen as a function of the angle of view and surface position.

8. The apparatus of any one of the previous claims wherein said spectral analyzer comprises a grating spectrometer.

9. The apparatus of claim 8 wherein said spectrometer provides a pattern representing the intensity of light from said emission as a function of wavelength.

10. The apparatus of any claim 9 wherein said first reflective surface includes an effector operative to move said first surface along an axis passing near or through said specimen and said at least one lens thereby causing the pattern of intensity of light to shift as a function of wavelength.

11. The apparatus of any claim 1 wherein said first reflective surface is spherical with a center substantially corresponding to a location of said specimen.

12. The apparatus of claim 1 wherein said specimen is a biological specimen and said emissions are from a marker associated with said specimen.

13. The apparatus of claim 3 wherein said radiation is laser radiation.

14. Apparatus for providing tomographic data representations of at least one specimen from optical interference patterns, said at least one specimen having an optical emission associated therewith, comprising:
   an optical system for receiving light emission from said specimen over a range of angles;
   a first reflective surface responsive to a portion of the emission from said specimen to redirect it toward said optical system to provide self interference of light in said emission;
   a radiation source;
   a second reflective surface responsive to said radiation from said source to provide an interference pattern in an environment of said specimen, said first reflective surface being disposed between said second reflective surface and said specimen;
   means for moving the first and second reflective surfaces to vary the position of said interference pattern in the environment of said specimen and to vary the interference pattern of the self interference; and
   a wavelength analyzer providing said tomographic representations as a function of the self interfering emission and the positions of said first and second reflective surfaces.

15. The apparatus of claim 14 wherein said first and second surfaces are focussing.

16. The apparatus of claim 15 wherein said optical system is configured to apply said source radiation to said specimen environment and to rotate an angle of application and receipt of radiation applied to said specimen and received from said specimen.

17. The apparatus of claim 16 wherein said optical system includes first and second lenses for receiving the radiation from the source and directing it to said specimen and for receiving emissions from the environment of said specimen.

18. The apparatus of claim 17 wherein at least one of said first and second reflective surfaces are movable in a direction along an axis which includes said specimen.

19. A method for determining the position of at least one specimen in an environment, comprising the steps of:
   supporting said specimen in a location a distance from a first reflective surface;
   said specimen having light emission associated therewith; and
   spectrally analyzing light representing the interference of the specimen emission associated with said specimen on paths directly from said at least one specimen and after reflection by said first reflective surface to provide an interference pattern resolvable for position of said specimen.

20. The method of claim 19 further including providing radiation for said specimen to excite said emission of said specimen.

21. The method of claim 19 wherein said specimen emissions are characterized by one or more of spontaneous emission, excitation induced emissions, self emissions of said specimen, and decaying emissions from previously excited emissions.

22. The method of claim 19 further including the steps of:
   moving at least one of said first reflective surface and a second reflective surface, said first reflective surface being disposed between said second reflective surface and said specimen;
   moving an angle of view through which said analyzer responds to said emissions; and providing a tomographic representation of the environment of said specimen as a function of the angle of view and surface position.

23. The method of claim 19 further providing a pattern representing the intensity of light from said emission as a function of wavelength.

24. The method of claim 19 further including moving said first reflective surface along an axis passing near or through said specimen thereby causing the pattern of intensity of light to shift as a function of wavelength.

25. The method of claim 19 wherein said specimen is a biological specimen and said emission is from a marker associated with said specimen.

26. A method for providing tomographic data representations of specimens from optical interference patterns, comprising the steps of:
receiving at an optical system light emission from a specimen over a range of angles;
responding to a portion of the emission from said specimen by a first reflective surface to redirect said portion toward said optical system to provide self interference of light in said emission in said optical system;
providing with a second reflective surface an interference pattern in an environment of said specimen, said first reflective surface being disposed between said second reflective surface and said specimen;
moving at least one of said first and second reflective surfaces to vary the position of said interference pattern in the environment of said specimen and to vary the interference pattern of the self interference; and
providing said tomographic representations as a function of the self interfering emission and the positions of said first and second reflective surfaces.

27. The method of claim 26 wherein said optical system is configured to apply said source radiation to said specimen environment and including the step of rotating an angle of application and receipt the radiation applied to said specimen and received from said specimen.

28. The method claim 27 including moving at least one of said first and second reflective surfaces in a direction along an axis which includes said specimen.

* * * * *

UNITED STATES PATENT AND TRADEMARK OFFICE
CERTIFICATE OF CORRECTION

PATENT NO.       : 7,110,118 B2                                              Page 1 of 1
APPLICATION NO.  : 10/451096
DATED            : September 19, 2006
INVENTOR(S)      : Selim M. Ünlü et al.

It is certified that error appears in the above-identified patent and that said Letters Patent is hereby corrected as shown below:

Title page, Item (75) Inventors, "Samuel Lipolf" should read --Samuel Lipoff--.

Signed and Sealed this

Second Day of October, 2007

JON W. DUDAS
*Director of the United States Patent and Trademark Office*